(12) United States Patent
Diamond

(10) Patent No.: US 11,821,890 B2
(45) Date of Patent: Nov. 21, 2023

(54) NANOSENSOR CHIP WITH COMPOUND NANOPORES AND METHODS OF USE THEREOF

(71) Applicant: Pinpoint Science Inc., San Francisco, CA (US)

(72) Inventor: Lisa Diamond, Alameda, CA (US)

(73) Assignee: Pinpoint Science Inc., San Francisco, CA (US)

( * ) Notice: Subject to any disclaimer, the term of this patent is extended or adjusted under 35 U.S.C. 154(b) by 0 days.

(21) Appl. No.: 17/145,954

(22) Filed: Jan. 11, 2021

(65) Prior Publication Data

US 2021/0220820 A1   Jul. 22, 2021

Related U.S. Application Data

(63) Continuation of application No. PCT/US2020/027550, filed on Apr. 9, 2020, which is
(Continued)

(51) Int. Cl.
*G01N 33/487* (2006.01)
*G01N 27/12* (2006.01)
*B01L 3/00* (2006.01)

(52) U.S. Cl.
CPC ...... *G01N 33/48721* (2013.01); *B01L 3/5025* (2013.01); *B01L 3/5027* (2013.01);
(Continued)

(58) Field of Classification Search
CPC .......... B01L 3/5025; B01L 3/5027; B01L 2300/0636; B01L 2300/0896;
(Continued)

(56) References Cited

U.S. PATENT DOCUMENTS 3,941,567 A * 3/1976 Combaz ............... G01N 30/12
359/398
7,851,203 B2   12/2010 Létant et al.
(Continued)

FOREIGN PATENT DOCUMENTS

CN           107135657 A    9/2017
WO    WO-2012073009 A2    6/2012
(Continued)

OTHER PUBLICATIONS

Malekian et al. (Frontiers in Chemistry, Dec. 2018, vol. 6 Article 637 (Year: 2018).*
(Continued)

*Primary Examiner* — Matthew D Krcha
*Assistant Examiner* — Jacqueline Brazin
(74) *Attorney, Agent, or Firm* — Wilson Sonsini Goodrich & Rosati

(57) ABSTRACT

Described herein are systems and methods of providing a nanosensor chip for detecting and/or quantifying target molecules in a solution. Said nanosensor chip comprises a pore comprising a plurality of nanopores. Said plurality of nanopores is functionalized with immobilized probe molecules for detecting the target molecules. The solution is directed to the nanochip to permit binding of said target molecules. Changes an aggregate current in response to target molecules in the liquid sample binding to the probe molecules are measured to detect and/or quantify said target molecules in said solution.

28 Claims, 6 Drawing Sheets

Related U.S. Application Data a continuation of application No. 16/383,491, filed on Apr. 12, 2019, now abandoned.

(52) U.S. Cl.
CPC ........ *G01N 27/128* (2013.01); *B01L 2200/10* (2013.01); *B01L 2300/0636* (2013.01); *B01L 2300/0896* (2013.01); *C12Q 2563/00* (2013.01); *C12Q 2563/116* (2013.01); *C12Q 2565/50* (2013.01); *C12Q 2565/60* (2013.01)

(58) Field of Classification Search
CPC .......... B01L 2200/10; G01N 33/48721; G01N 27/128; C12Q 2563/00; C12Q 2563/116; C12Q 2565/50; C12Q 2565/60
USPC ...................................................... 435/287.2
See application file for complete search history.

(56) References Cited

U.S. PATENT DOCUMENTS

| | | | |
|---|---|---|---|
| 8,377,717 | B2 | 2/2013 | Bright |
| 8,592,225 | B2 | 11/2013 | Ronaghi et al. |
| 8,940,142 | B2 | 1/2015 | Karhanek et al. |
| 8,980,073 | B2 | 3/2015 | Pourmand et al. |
| 9,057,719 | B2 | 6/2015 | Pei et al. |
| 9,121,843 | B2 | 9/2015 | Meller et al. |
| 9,326,716 | B2 | 5/2016 | Heller et al. |
| 9,624,537 | B2 | 4/2017 | Huber et al. |
| 9,675,708 | B2 | 6/2017 | Aprikyan et al. |
| 9,816,988 | B1 | 11/2017 | Paik et al. |
| 10,006,905 | B2 | 6/2018 | Maglia et al. |
| 2005/0074778 | A1 | 4/2005 | Letant et al. |
| 2005/0127035 | A1 | 6/2005 | Ling |
| 2006/0210995 | A1 | 9/2006 | Joyce |
| 2007/0138132 | A1 | 6/2007 | Barth |
| 2010/0066348 | A1 | 3/2010 | Merz et al. |
| 2013/0164219 | A1 | 6/2013 | Brinkmann et al. |
| 2013/0180867 | A1 | 7/2013 | Rosenstein et al. |
| 2013/0260371 | A1 | 10/2013 | Holt |
| 2014/0318968 | A1 | 10/2014 | Luan et al. |
| 2015/0060952 | A1 | 3/2015 | Takulapalli et al. |
| 2015/0111779 | A1 | 4/2015 | Davis |
| 2015/0119259 | A1* | 4/2015 | Ju .................. C12Q 1/6869 506/2 |
| 2015/0177237 | A1 | 6/2015 | Turner et al. |
| 2015/0301015 | A1 | 10/2015 | Fordham et al. |
| 2016/0178576 | A1 | 6/2016 | Maney et al. |
| 2016/0282326 | A1 | 9/2016 | Waduge et al. |
| 2017/0058336 | A1 | 3/2017 | Ivankin et al. |
| 2017/0268054 | A1* | 9/2017 | Akahori .......... G01N 33/48721 |
| 2017/0315109 | A1* | 11/2017 | Alden .................. C12Q 1/6869 |
| 2018/0045675 | A1 | 2/2018 | Ozel et al. |
| 2018/0164205 | A1 | 6/2018 | Edel et al. |
| 2018/0335417 | A1 | 11/2018 | Goto et al. |
| 2019/0004029 | A1 | 1/2019 | Branton et al. |
| 2019/0064157 | A1 | 2/2019 | Miyagawa et al. |
| 2019/0383789 | A1* | 12/2019 | Leburton ............... B82Y 15/00 |
| 2020/0033319 | A1* | 1/2020 | Karimirad ............ C12Q 1/6869 |
| 2020/0326325 | A1 | 10/2020 | Diamond |

FOREIGN PATENT DOCUMENTS

| | | | | |
|---|---|---|---|---|
| WO | WO-2014100693 | A1 | 6/2014 | |
| WO | WO-2017100683 | A1 | 6/2017 | |
| WO | WO-2017184790 | A1 | 10/2017 | |
| WO | WO-2019026359 | A1 * | 2/2019 | .............. C12M 1/00 |
| WO | WO-2020210548 | A1 | 10/2020 | |

OTHER PUBLICATIONS

U.S. Appl. No. 16/383,491 Office Action dated Apr. 22, 2020.
U.S. Appl. No. 16/383,491 Office Action dated Dec. 10, 2019.
U.S. Appl. No. 16/383,491 Office Action dated Jul. 31, 2019.
U.S. Appl. No. 16/383,491 Office Action dated Nov. 3, 2020.
Actis, P. et al., "Voltage-controlled metal binding on polyelectrolyte functionalized nanopores," Langmuir, May 17, 2011, vol. 27, No. 10, pp. 6528-6533.
Ali, A. et al., "Single Cigar-Shaped Nanopores Functionalized with Amphoteric Amino Acid Chains: Experimental and Theoretical Characterization," American Chemical Society, 2012, vol. 6, No. 4, pp. 3631-3640.
Ali, M. et al., "Metal Ion Affinity-based Biomolecular Recognition and Conjugation inside Synthetic Polymer Nanopores Modified with Iron-Terpyridine Complexes," Journal of the American Chemical Society, 2011, vol. 133, No. 43, pp. 17307-17314.
Asghar, W. et al., "Electrical fingerprinting, 3D profiling and detection of tumor cells with solid-state micropores," Lab on a Chip, 2012, vol. 12, No. 13, pp. 2345-2352.
Briggs, K., "Solid-State Nanopores: Fabrication, Application, and Analysis," University of Ottawa, 2018, pp. 1-300.
Bulbul, G. et al., "Nanopipettes as Monitoring Probes for the Single Living Cell: State of the Art and Future Directions in Molecular Biology," Cells, Jun. 6, 2018, vol. 7, No. 55, pp. 1-21.
Chuah, K. et al., "Nanopore blockade sensors for ultrasensitive detection of proteins in complex biological samples," Nature Communications, 2019, vol. 10, pp. 1-9.
Dekker, C., "Solid-state nanopores," Nature Nanotechnology, 2007, pp. 1-7.
Ellis, J.S. et al., "Electrochemical Characterization of Regularly-aligned Nanopore Array Membranes Filled with Electrolyte Solutions and their use for Detection of Nucleic Acid Hybridization," ECS Transactions, 2011, vol. 35, No. 7, pp. 1-16.
Gadaleta, A. et al., "Sub-additive ionic transport across arrays of solid-state nanopores," Physics of Fluids, 2014, vol. 26, No. 1, pp. 012005.
Liu, L. et al., "Detecting a single molecule using a micropore-nanopore hybrid chip," Nanoscale Research Letters, 2013, vol. 8, No. 1, pp. 498.
Lo, C.J. et al., "Fabrication of symmetric sub-5 nm nanopores using focused ion and electron beams," Nanotechnology, 2006, vol. 17, No. 13, pp. 3264-3267.
PCT International Search Report and Written Opinion, PCT Application No. PCT/US20/27550, dated Jul. 6, 2020, 17 pages.
Pitchford, W.H. et al., "Synchronized Optical and Electronic Detection of Biomolecules Using a Low Noise Nanopore Platform," American Chemical Society, 2015, vol. 9, No. 2, pp. 1740-1748.
Ramirez, P. et al., "Pore structure and function of synthetic nanopores with fixed charges: tip shape and rectification properties," Nanotechnology, 2008, vol. 19, No. 31, pp. 315707.
Raza, M.U. et al., "Crosstalk between adjacent nanopores in a solid-state membrane array for multi-analyte high-throughput biomolecule detection," Journal of Applied Physics, 2016, vol. 120, pp. 064701-1-064701-8.
Stroeve, P. et al., "Biotechnical and other applications of nanoporous membranes," Trends in Biotechnology, 2011, vol. 29, No. 6, pp. 259-266.
Talasaz, A.A.H. et al., "Modeling of the Bioactivated Nanopore Devices," Proceedings of the 28th IEEE EMBS Annual Conference, 2006, pp. 1830-1833.
Umehara, S. et al., "Label-free biosensing with functionalized nanopipette probes," PNAS, Mar. 24, 2009, vol. 106, No. 12, pp. 4611-4616.
Waduge, P. et al., "Programmed Synthesis of Freestanding Graphene Nanomembrane Arrays," Small, 2015, No. 5, pp. 597-603.
EP20787831.5 extended European search report dated Dec. 8, 2022.

* cited by examiner

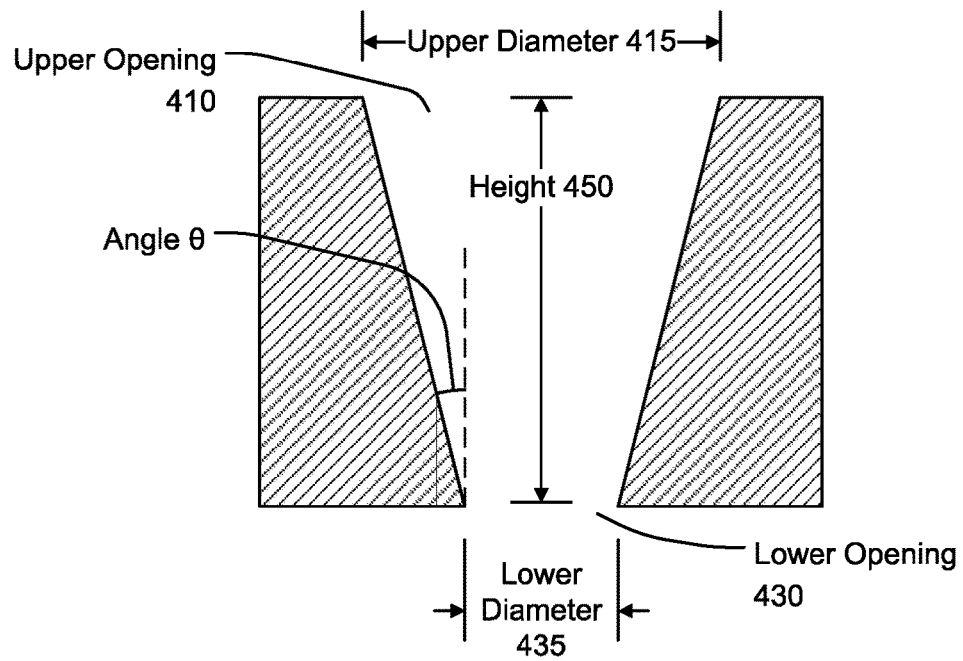
FIG. 4
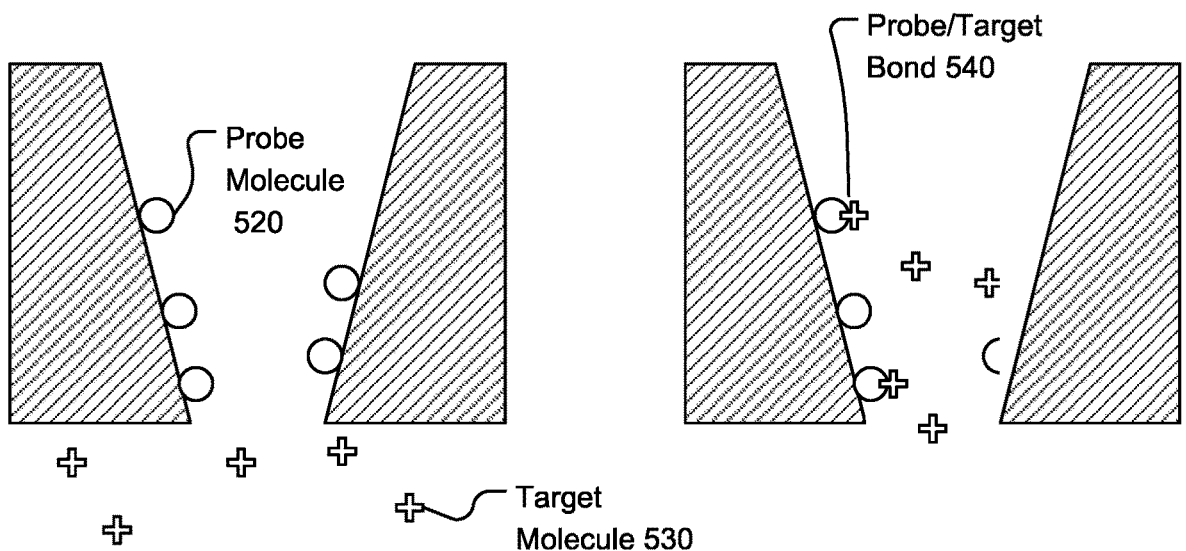
FIG. 5A  FIG. 5B

ABSTRACT

NANOSENSOR CHIP WITH COMPOUND NANOPORES AND METHODS OF USE THEREOF

CROSS-REFERENCE TO RELATED APPLICATIONS

This application is a continuation application of International Application No. PCT/US2020/027550, filed Apr. 9, 2020, the entirety of which is incorporated by reference herein.

BACKGROUND

Nanopipettes have been developed to detect biomolecules in a liquid sample. Current nanopipette sensors have a single funnel-shaped structure with probe molecules on the inner wall of the structure. The nanopipette sensor is immersed in a liquid sample, and an electric field is applied to the sensor. Target molecules bind to the probe molecules when the electric field is applied at a specific voltage. This binding causes a detectable current change across the nanopipette sensor.

Current nanopipette sensors fashioned from quartz glass capillary tubes suffer from significant shortcomings. They are difficult to fabricate and manufacture at scale. They are also fragile and easily broken. In addition, individual nanopipettes are highly variable and must be individually calibrated for accurate results. Nanopipette tips also show chemical and electrical degradation after repeated use, which seriously compromises performance and limits reuse.

SUMMARY

A nanosensor chip for detecting and/or quantifying target molecules in a liquid sample is disclosed herein. The nanosensor chip includes a semiconductor substrate with one or more compound nanopores formed in the semiconductor substrate. Each compound nanopore is an aperture that includes multiple nanopores, each of which is functionalized with immobilized probe molecules. The probe molecules are used to detect the target molecules in the liquid sample. A compound nanopore is referred to herein as a "compore."

Each compore has a corresponding electrode structure on the semiconductor substrate. The electrode structure has a shape and position relative to the compore that enable the electrode structure to apply an electric field across all of the nanopores in the compore. The electrode structure also provides a conductive path for detecting an aggregate current through all of the nanopores in the compore. The detected aggregate current changes in response to target molecules in the liquid sample binding to the probe molecules, which binding is a function of the applied electric field.

For example, if the liquid sample includes some of the target molecules (e.g., a particular viral protein in a biofluid sample), when a specific electric field (or voltage) is applied across the compore, the target molecules bind to probe molecules in the nanopores. The probe molecules that functionalize the compore are selected to bind to the particular target molecule when a specific electric field is applied. The binding of the target molecules to the probe molecules changes the electrical characteristics of the nanopore openings, which creates a change in the aggregate current through the compore. A given probe molecule-target molecule pairing binds in the presence of a particular electric field strength or range of electric field strengths. If the liquid sample does not include the target molecule and the electric field is applied, there will be no aggregate current change. In addition, if an electric field different from the particular electric field strength or range is applied, the target molecules do not bind to the probe molecules and there is no aggregate current change.

The compore structure provides a greater level of reliability than prior nanopipette sensors. For example, if one of the nanopores in the compore is blocked or clogged, an aggregate current change is detected based on the binding of the target molecules to the probe molecules in the other, unblocked nanopores. Furthermore, if the nanopores in a given compore are not uniformly functionalized with the probe molecules, e.g., some nanopores have a higher concentration of probe molecules and other nanopores have a lower concentration of probe molecules, the change in aggregate current across all of the nanopores averages out the variations in concentration when detecting the presence of target molecules in liquid sample. Because of this greater reliability, the compore sensor is more accurate and reliable than prior nanopipette sensors.

Nanosensor chips may have other advantages over nanopipette technology. In particular, nanosensor chips can be efficiently and inexpensively manufactured at scale. An entire wafer of chips may be functionalized with probe molecules simultaneously, where the prior nanopipettes are individually functionalized. Due to improved consistency, a single chip can be used to calibrate an entire wafer of chips, instead of individually calibrating the nanopipettes.

Other aspects include components, devices, systems, improvements, methods, processes, applications, and other technologies related to any of the above.

BRIEF DESCRIPTION OF THE DRAWINGS

FIG. 4 is a cross-section of a single nanopore within a compore.

FIGS. 5A and 5B are cross-sections that show operation of a nanopore.

DETAILED DESCRIPTION

The Figures (FIGs.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed nanosensor chip for purposes of illustration only. One skilled in the art will readily recognize from the following description that alternative embodiments of the structures and methods illustrated herein may be employed without departing from the principles described herein.

Figure 1:
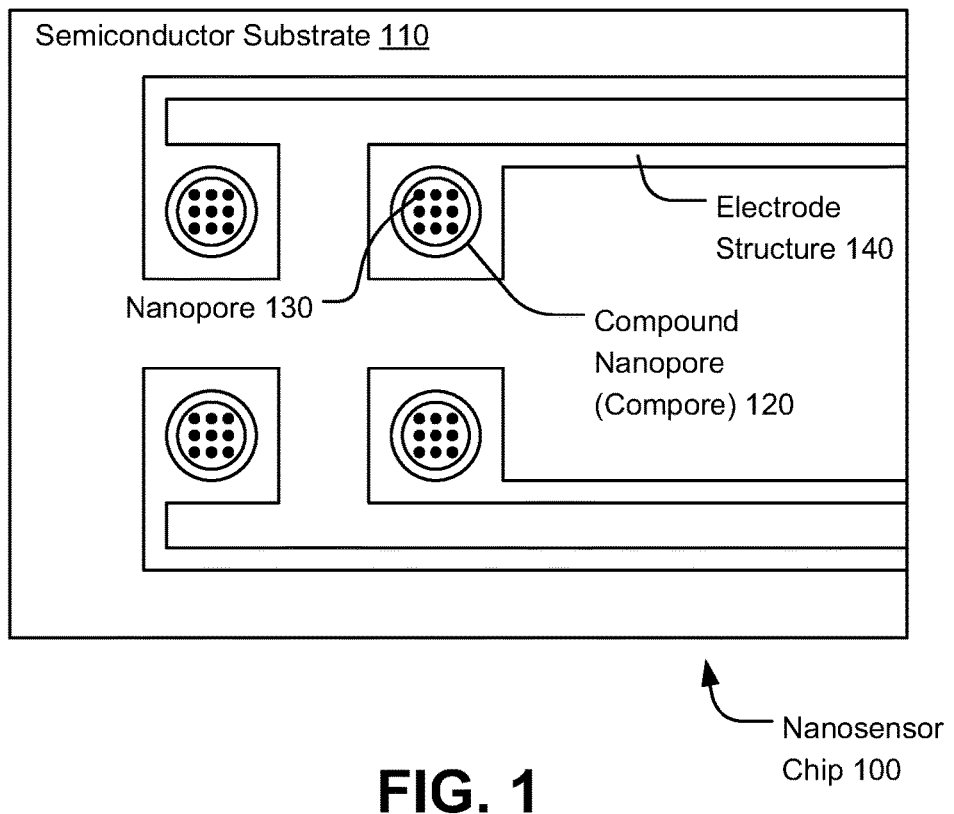
FIG. 1 is a top view of a nanosensor chip with multiple compores.

FIG. 1 is a top view of a nanosensor chip 100 with multiple conical compound nanopores 120, also referred to as compores 120. The nanosensor chip 100 is formed from a semiconductor substrate 110, e.g., a silicon or gallium arsenide (GaAs) substrate. Alternative substrates can be used instead, such as glass, plastic, film and other materials. One or more compores 120 are formed in the semiconductor substrate 110. A compore 120 is an aperture formed in the semiconductor substrate 110 that includes multiple nanopores 130. The nanopores 130 form holes extending through the semiconductor substrate 110. The nanopores 130 have openings at a top of the compore 120 (shown in FIG. 1) and at a bottom of the compore 120 on the reverse side of the nanosensor chip 100 (not visible in FIG. 1). The nanopores 130 of the compore 120 are functionalized with immobilized probe molecules and collectively form an aperture through the semiconductor substrate 110. The compore 120 may have a maximum width between 1 micron and 1000 microns. The compore 120 is brought into contact with a liquid sample, for example it may be positioned vertically between sample and buffer reservoirs. It can be used to detect whether or not one or more target molecules are present in the liquid sample and/or to quantify the concentration of target molecules in the liquid sample, based on binding of the target molecules to the probe molecules.

The compore 120 can be used to assay any liquid sample, e.g., a sample of blood, saliva, spinal liquid, urine, food, beverage, water, etc., in which a target molecule of interest may be present. Different nanosensor chips 100, and different compores 120 within a single nanosensor chip 100, may be configured to assay different types of liquid samples and to detect one or more types of target molecules within the liquid sample. For example, one nanosensor chip 100 may be configured to test for a set of antibodies in blood samples, while another nanosensor chip 100 is configured to test for a set of contaminants in water samples.

Each of the nanopores 130 in a compore 120 is functionalized with immobilized probe molecules. Each nanopore 130 has a sidewall extending between the two openings, and probe molecules are affixed to the sidewall of the nanopore 130. An example arrangement of probe molecules within a nanopore 130 is shown in FIGS. 5A and 5B. The probe molecules may be selected for detecting a particular type of target molecule or set of target molecules in a liquid sample, e.g., to detect a particular antibody or set of antibodies in a blood sample, or to detect a particular contaminant in water. The probe molecules have a binding affinity to the target molecules, such that in the presence of a specific electric field, target molecules in a sample bind to the probe molecules. The target molecules may reversibly bind to the probe molecules, so that when the electric field is removed, the target molecules release from the probe molecules. Examples of probe molecules include antibodies, antibody analogs, proteins, aptamers, polymers, oligonucleotides, and nanobodies.

Figure 9:
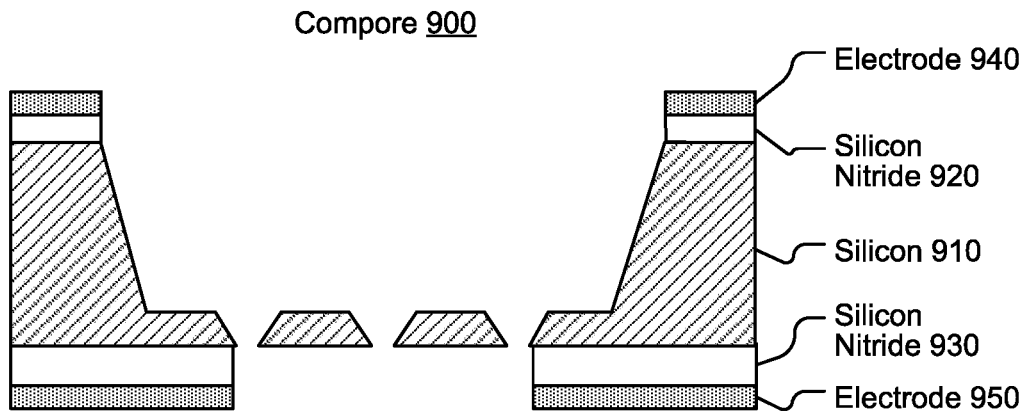
FIG. 9 is a cross-section of a compore fabricated using semiconductor technology.

Each compore 120 has a corresponding electrode structure 140 laid out on the semiconductor substrate 110. The electrode structure 140 has a shape and a position relative to the compore 120 suitable to apply an electric field across all of the nanopores 130 in the compore 120. The electrode structure 140 also provides a conductive path for conducting an aggregate current that passes through the nanopores 130 in the compore 120. For example, the electrode structure 140 may include one or more electrodes on the top of the compore 120 (as shown in FIG. 1) and one or more electrodes on the reverse side of the compore 120 (not visible in FIG. 1). Exemplary electrode structures are shown in FIGS. 3 and 9. The electrode structure 140 may connect to circuitry located on the nanosensor chip 100 for supplying a voltage source for the electric field and/or detecting the aggregate current. Alternatively, the electrode structure 140 may connect to an off-chip source and/or detector.

When the liquid sample includes the target molecule and the correct electric field is applied across the compore 120, the target molecules bind to the immobilized probe molecules in the nanopores 130. This binding changes an aggregate current that passes through the compore 120. The aggregate current flows through the electrode structure 140 to a current detector on the nanosensor chip 100 or connected to the nanosensor chip 100. A change in the aggregate current through all of the nanopores 130 of a compore 120 indicates the presence of the target molecules in the liquid sample. An amount by which the aggregate current changes may be used to determine a concentration or quantity of the target molecules in the liquid sample. By contrast, if the particular electric field is applied to the compore 120 but no aggregate current change is detected, this indicates that the target molecules are not present in the liquid sample.

Because each compore 120 includes multiple nanopores 130 that experience the same electric field and the aggregate current through all of the nanopores is detected, the compore 120 has a greater reliability than previous nanosensors. For example, even if one or a few of the nanopores 130 are blocked or clogged, the aggregate current through the set of nanopores 130 in the compore 120 still changes in response to the target molecules in the liquid sample binding to the probe molecules in the presence of the electric field. Similarly, the change in aggregate current through the set of nanopores 130 can still be detected even if the nanopores are not uniformly functionalized, e.g., if some nanopores have more immobilized probe molecules than other nanopores. In addition, using multiple nanopores 130 increases the number of different types of target molecules that a single compore 120 can be used to detect, because the nanopores 130 can be functionalized with multiple different types of probe molecules. Configurations with multiple types of probe molecules are described further in relation to FIGS. 5A and 5B.

The nanosensor chip 100 depicted in FIG. 1 includes four compores 120. In other arrangements, the nanosensor chip 100 may include any number of compores, e.g., one, four, sixteen, or many hundreds or even thousands of compores. Two compores 120 on the nanosensor chip 100 may test the same liquid sample or different liquid samples. The compores on the nanosensor chip 100 may be identical, or some or all of the compores may be different from each other. For example, two compores 120 on a single nanosensor chip 100 may have different sizes, different shapes, different numbers of nanopores, nanopores with different sizes or shapes, or nanopores with different probe molecules. Including different compores on a single nanosensor chip 100 enables a single nanosensor chip 100 to perform multiple different tests, e.g., to test for multiple different target molecules, to test with different sensitivities, or to include controls to verify the accuracy and to authenticate the nanosensor chip 100. Including multiple identical compores on a single nanosensor chip 100 may be used to improve the accuracy and reliability of a single nanosensor chip 100.

In FIG. 1, each compore 120 on the nanosensor chip 100 may be individually addressed using its respective electrode structure 140. Because each compore 120 has a separate electrode structure 140, the aggregate current through each compore 120 can be individually measured by a current detector connected to the electrode structure 140. In some embodiments, each electrode structure 140 is also used to individually apply an electric field across each respective compore 120. In other embodiments, the electrode structure for applying the electric field across a compore is distinct from the electrode structure used to measure the aggregate current through a compore. In such embodiments, the electrode structures for applying the electric fields may be connected for two or more compores, so that the same electric field or voltage can be applied to multiple compores simultaneously.

Figure 2:
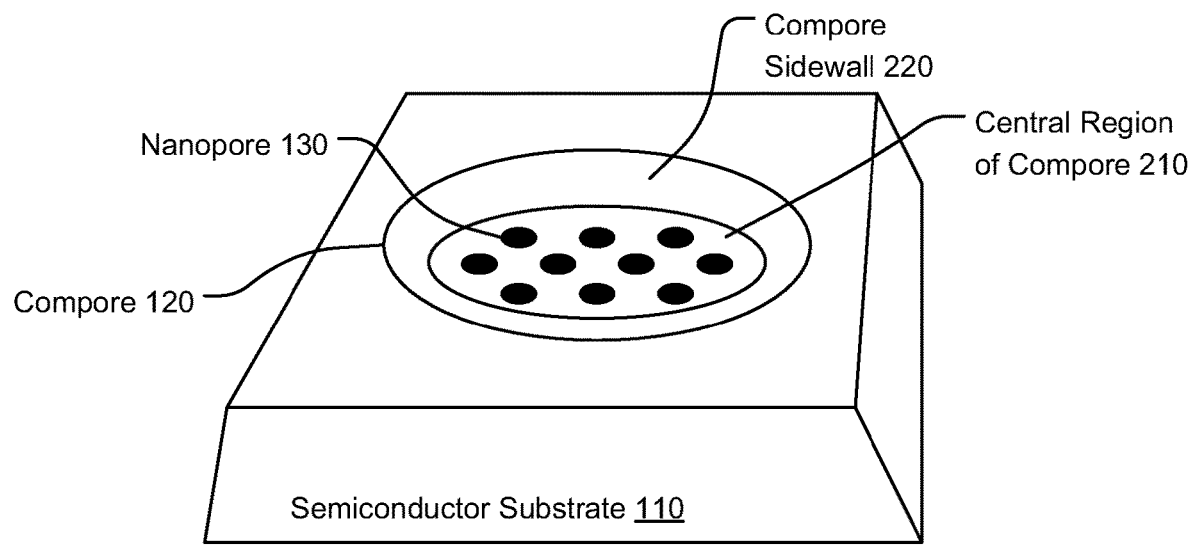
FIG. 2 is a perspective view of an individual compore.

FIG. 2 is a perspective view of an individual compore 120, but not showing the electrode structure. FIG. 2 shows the structure of the compore 120 in greater detail. The compore 120 has a central region 210 that is thinner than the semiconductor substrate 110. The nanopores 130 are formed within this thinned central region. For example, the central region 210 may be thinned to a thickness of less than 1 micron. The thickness of the central region 210 is also the height of the nanopores 130 formed within the compore 120. In a nanosensor chip with multiple compores, such as the nanosensor chip 100 shown in FIG. 1, the thinned regions of the compores are separated from each other by unthinned regions. If desired, this may be used to maintain separation between the liquid samples of different compores and to maintain isolation between the voltages and currents of different compores.

Between the top of the central region 210 and the top of the semiconductor substrate 110, the compore 120 has a compore sidewall 220. The compore sidewall 220 is depicted as being sloped, but it may be straight, curved, or have some other arrangement. In some embodiments, the liquid sample may be placed in the depression formed by the central region 210 and the compore sidewall 220, with a buffer solution on the other side of the compore 120. In other embodiments, the nanosensor chip 100 may be positioned vertically between two reservoirs, one containing buffer solution and the other containing the liquid sample.

Various other configurations for applying a liquid sample to the compore 120 may be used. For example, the opposite side of the compore 120 may be exposed to the liquid sample instead. In such embodiments, the portion of the compore 120 surrounded by the compore sidewall 220 may receive a liquid buffer.

Figure 3A:
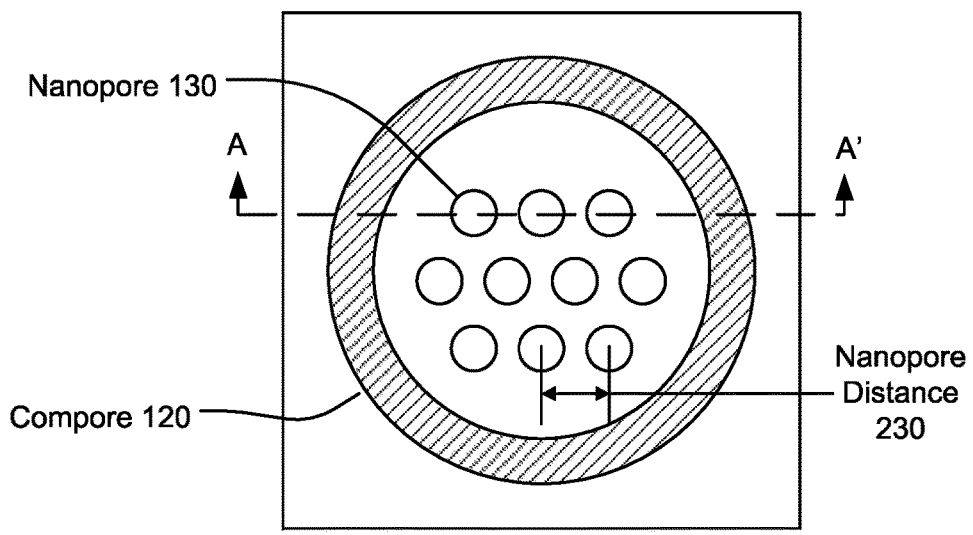
FIG. 3A is a top view of an individual compore.

FIG. 3A is a top view of an individual compore 120. FIG. 3A shows an exemplary arrangement of nanopores 130 in a compore 120. Adjacent nanopores 130 are separated by some spacing 230. The spacing distance 230 between two adjacent nanopores in a single compore 120 may be, for example, between 1 nanometer and 100 microns. In the example shown in FIG. 3A, the compore 120 has ten nanopores 130. In other embodiments, a compore 120 may have a different number of nanopores 130, e.g., from two to several hundred nanopores. While the nanopores 130 in FIG. 3A shows the nanopores 130 being arranged in three rows, in other embodiments, the nanopores 130 may have a different arrangement.

Figure 3B:
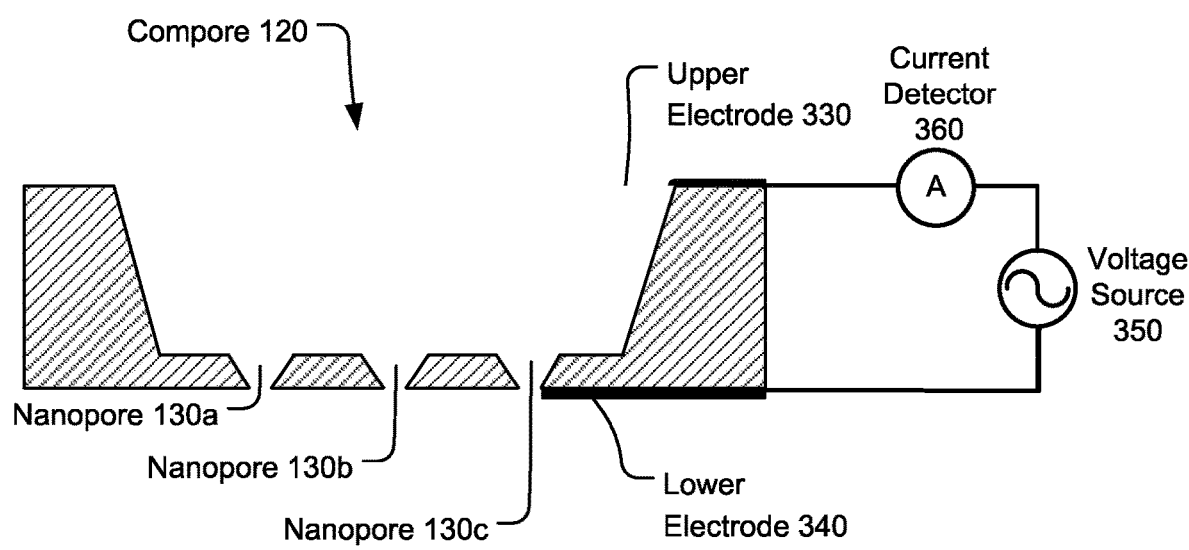
FIG. 3B is a cross section of the compore shown in FIG. 3A.

FIG. 3B is a cross section of the compore 120 through line A-A' shown in FIG. 3A. The compore cross-section includes three nanopores 130a, 130b, and 130c that pass through the semiconductor substrate 110. In this embodiment, one side of the nanopore structure is characterized by a depression formed by the top of the thinner central region and the compore sidewalls. For convenience, this side will be referred to as the top side, and the reverse side will be referred to as the bottom side. Either the top side or the bottom side may be exposed to the liquid sample, and the other side is typically exposed to a buffer. In FIG. 3B, an upper electrode 330 is formed on the top surface of the compore 120 and a lower electrode 340 is formed on the bottom surface. However, one or both of these electrodes may be mounted externally to the chip, e.g. in the chip receptacle, in alternative embodiments.

The upper electrode 330 and lower electrode 340 form the electrode structure for applying the electric field to the compore 120 and for conducting the aggregate current through the nanopores 130. Because all of the nanopores 130 in the compore 120 are in close proximity to each other, the electrode structure comprising the upper electrode 330 and lower electrode 340 located to the side of the nanopores 130 may be sufficient to apply an electric field across all of the nanopores 130 and to detect an aggregate current through all of the nanopores 130. In alternative embodiments, the electrode structure may be more complex. For example, the upper electrode 330 may have a portion to the left of the nanopore 130a or encircling all of the nanopores (as shown in FIG. 1). The upper electrode 330 may also extend into the areas between the nanopores 130a-130c. Similarly, the lower electrode 340 may have an additional portion formed to the left of the nanopore 130a, encircling the nanopores, and/or extending into the areas between the nanopores 130a-130c.

The upper electrode 330 and lower electrode 340 are connected to a voltage source 350 and a current detector 360. The voltage source 350 supplies a selected voltage to the upper and lower electrodes 340, which creates the electric field across all of the nanopores 130 in the compore 120. The current detector 360 detects the aggregate current flowing through all the nanopores 130 in the compore 120. The voltage source 350 and the current detector 360 may use different electrodes.

In some embodiments, the voltage source 350 and/or current detector 360 are incorporated into the nanosensor chip 100. In such embodiments, the nanosensor chip 100 may further include a controller for controlling the voltage source 350 and the current detector 360. For example, the controller may control the voltage source 350 to vary the applied voltage, in amplitude or frequency. Different patterns of applied voltages (i.e., electric fields) may be used to probe for different target molecules. From the current detector 360, the controller may determine whether there is a change in the measured aggregate current through the compore 120 as a function of the applied voltage. For example, the controller may instruct the voltage source 350 to apply a series of different voltages across the compore 120 and, for each voltage, detect a level of change in the measured aggregate current. The controller may generate a signal indicating the current detected by the current detector 360 or indicating the determined change in detected current and transmit this signal to an off-chip processor for further processing. The controller may be implemented on the nanosensor chip and/or as part of an external device or component.

FIG. 4 is a cross-section of a single nanopore 130 of the compore 120. The compore 130 has an upper opening 410 at the top of the nanopore 130 and a lower opening 430 at the bottom of the nanopore 130. The upper opening 410 has an upper diameter 415, and the lower opening 430 has a lower diameter 435. The upper diameter 420 may be in the range of 1 nanometers to 300 nanometers. In this example, the lower diameter 440 is smaller than the upper diameter 420, and may be less than 300 nanometers. However, in other embodiments, the nanopore may be "flipped" so that the upper opening is smaller. The nanopore 130 has a height 450, which is the same as the height of the thinned central region 210 of the nanopore. The height 450 of the nanopore may be 1 micron or less. The nanopore has a sidewall extending between the upper opening 410 and the lower opening 430. The sidewall slope is defined by the angle θ, which may be between 6° and 60°. In other embodiments, the sidewall is not straight as shown in FIG. 4, but may be curved or have some other shape.

FIGS. 5A and 5B are cross-sections that show operation of a nanopore. FIG. 5A shows a nanopore 130 having probe molecules 520 affixed to the sidewall. As shown in FIG. 5A, the probe molecules are affixed to the sidewall near the smaller opening, i.e., the lower opening 430 shown in FIG. 4. The probe molecules 520 may extend up the entire sidewall, or may be concentrated in a portion of the sidewall, e.g., along a lower portion of the sidewall near the lower opening 430. The probe molecules 520 may be attached to the sidewall of the nanopore 130 by covalent binding, non-covalent binding, or physisorption.

In the example shown in FIGS. 5A and 5B, the nanopore 130 is exposed to a liquid sample that includes a target molecule 530. In the example shown in FIG. 5A, the sample with the target molecule is located below the nanopores 130. As described above, in other embodiments, the sample containing the target molecule may be located on the other side of the nanopores 130. FIG. 5A shows the nanopore without the proper electric field applied. In this condition, the target molecules 530 remain separated from the probe molecules 520.

FIG. 5B shows the same nanopore after a specific electric field has been applied across the compore. In the presence of this electric field, the target molecules 530 are attracted inside the nanopore, and individual target molecules 530 bind to corresponding probe molecules 520 to form probe/target bonds 540. This binding creates an ionic current change in current across the nanopore 130. The other nanopores in the compore are also functionalized with the same probe molecules 520 and exposed to the same sample and electric field, so other target molecules 530 in the sample flow into the other nanopores to form additional probe/target bonds 540 across the compore. The probe/target bonds 540 across the nanopores of the compore create an aggregate ionic current change that is measurable by the current sensor.

When the electric field is removed or changed, the target molecules 530 release from the probe molecules 520. The target molecules 530 may flow out the nanopore 130, reverting to the arrangement shown in FIG. 5A. The probe/target bond 540 is reversible, so that when the compore is subjected to a varying voltage, the target molecules 530 continually bind and release from the probe molecules 520. The probe molecules 520 remain affixed to the sidewalls of the nanopores after use of the compore 120, e.g., after the target molecules 530 bind and then release, and through resetting the compore 120 with a buffer liquid. Because the probe molecules 520 remain affixed after use, the compore 120 can be reused for multiple samples.

For some applications, the nanopores of a single compore 120 are functionalized with two or more different probe molecules. The probe molecules may be a same category of molecule (e.g., two antibodies) or different categories of molecules (e.g., one antibody and one protein). This allows a single compore 120 to be used to detect multiple different types of target molecules. In one exemplary application, a first probe molecule pairs with a first target molecule at a first electric field strength (e.g., +0.2 volts), a second probe molecule pairs with a second target molecule at a second electric field strength (e.g., +0.4 volts), and a third probe molecule pairs with a third target molecule at a third electric field strength (e.g., +0.6 volts). A sequence of different electric fields can be applied to the compore 120 to determine if any of the three target molecules are present in the sample. This allows the compore 120 to be used to efficiently perform multiple tests simultaneously on a single sample with a single sensor.

For other applications, the probe molecules may be selected so that multiple target-probe pairings are able to bind at the same range of voltages. This configuration may be used to detect the presence of any of a set of target molecules, e.g., a set of multiple potential contaminants within a food product, or a set of target antibodies in a blood sample. By using multiple target-probe pairings that bind at the same voltage, the compore 120 can efficiently identify a negative result for a sample. For some applications, if a positive result is obtained, further testing may be performed to determine which target molecule is present after an initial positive result is obtained.

Including multiple nanopores 130 in a single compore 120 allows the compore 120 to be functionalized with more types of probe molecules than prior sensors. An entire wafer of nanosensor chips may be accurately spotted in parallel with probe molecules using a specialized high-resolution printer. This enables production of multiplex tests and test panels at low cost. Additionally, compores 120 may be functionalized to detect positive and negative controls for validation and calibration, as well as markers to authenticate and verify the integrity of the nanosensor chip and reagents.

Figure 6A:
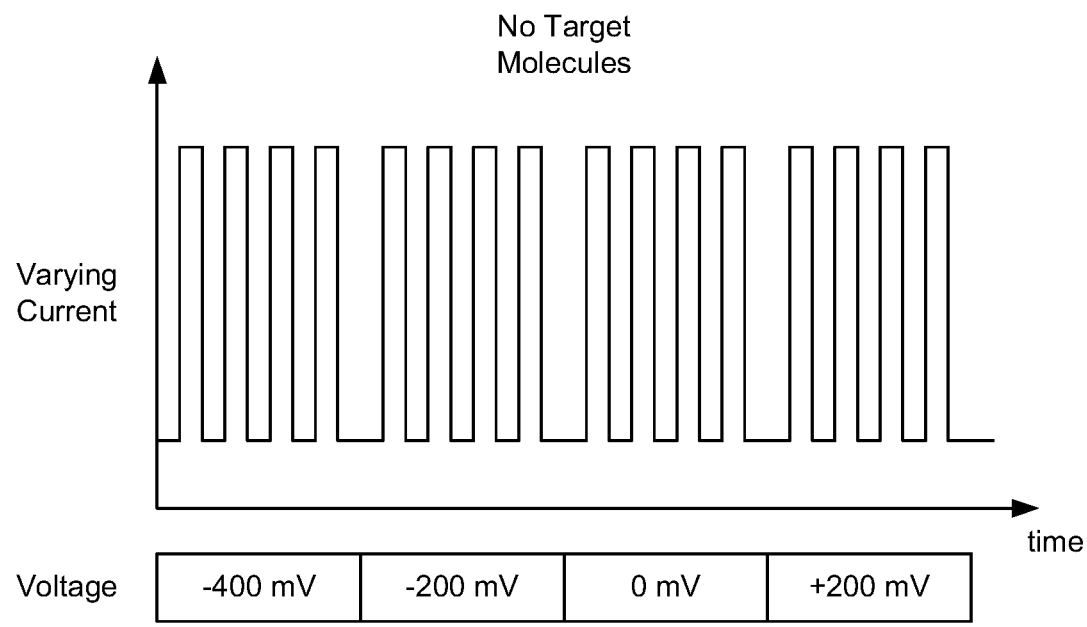
FIGS. 6A and 6B are graphs that illustrate operation of a compore.
Figure 6B:
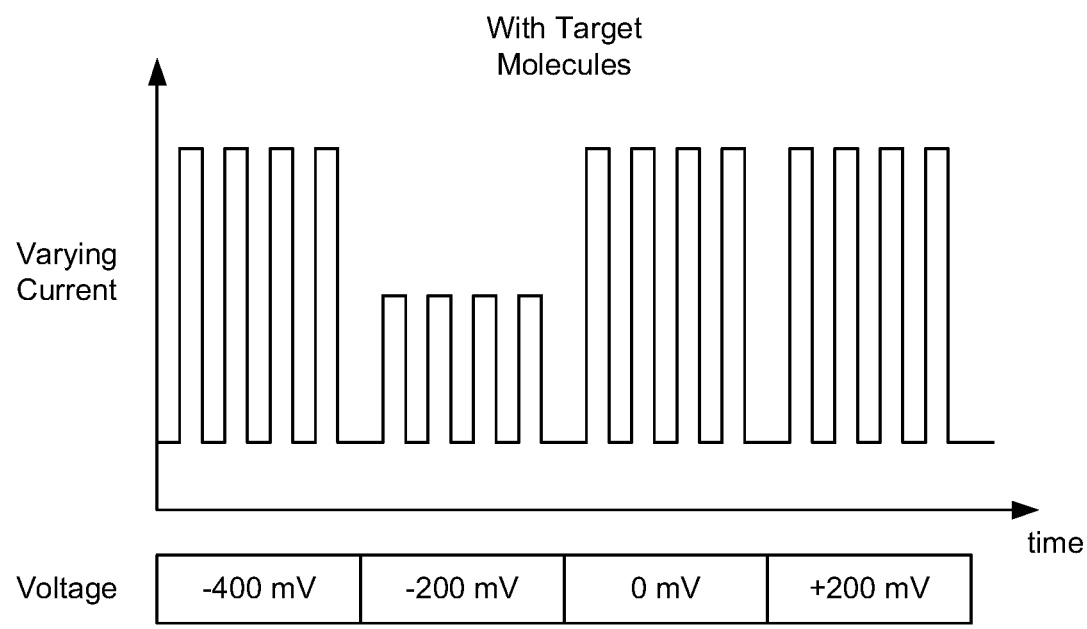

FIGS. 6A and 6B are graphs that illustrate operation of a compore. FIG. 6A is a graph showing the behavior of the compore when there are no target molecules present and FIG. 6B shows the response with target molecules. In this example, the voltage source 350 generates a square-wave current first at a voltage of −400 millivolts (mV), then at −200 mV, at 0 mV, and at +200 mV. Each specific pair of probe and target molecule will have a specific voltage at which they will bind. This changes the electrical characteristics of the nanopore 130 opening, which alters the current, as shown in FIG. 6B where the specific voltage is −200 mV. Compared to FIG. 6A, the strength of the output current changes. This indicates that the target molecules are binding to the probe molecules in the presence of the −200 mV electric field, so the target molecules that bind to probe molecules at −200 mV are present in the sample. The magnitude of the change in current may also indicate the concentration of target molecules in the sample. If a variable voltage is used, the target molecules may bind and release from the probe molecules. Certain target molecules may not bind and release. Instead, these may bind and remain bound.

Figure 7:
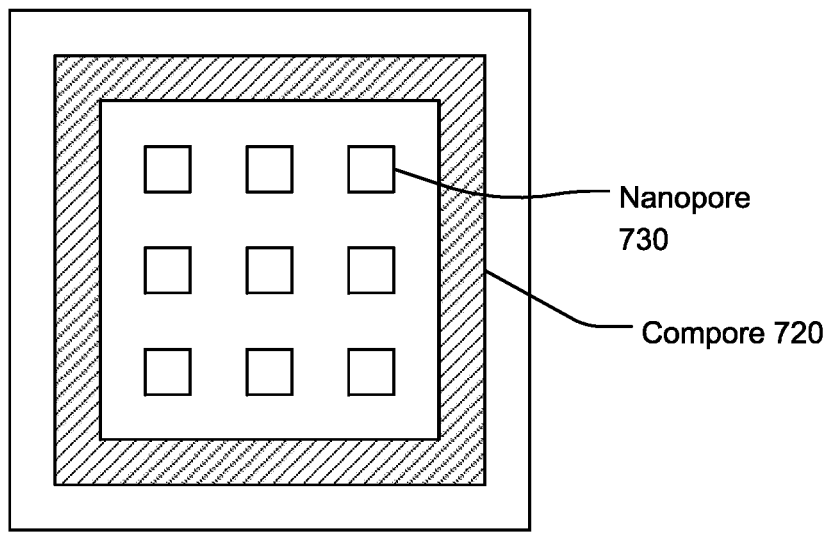
FIG. 7 is a top view showing a first alternative arrangement of nanopores within a compore.

While the compore 120 depicted in FIGS. 1-3 has a circular shape and circular nanopores 130, in other embodiments, the compore 120 and/or nanopores 130 may have different shapes and the nanopores may be arranged differently within the compore. FIG. 7 is a top view showing a first alternative arrangement of nanopores within a compore.

FIG. 7 depicts a square compore 720 that has square nanpores 730. In other embodiments, the compore 720 may be shaped as an oval, a rectangle, another polygon, or some other shape. Similarly, the nanopores 730 may be oval, rectangular, some other polygon, or have some other shape. The shape of the nanopores 730 may be different from the shape of the compore 720.

Figure 8:
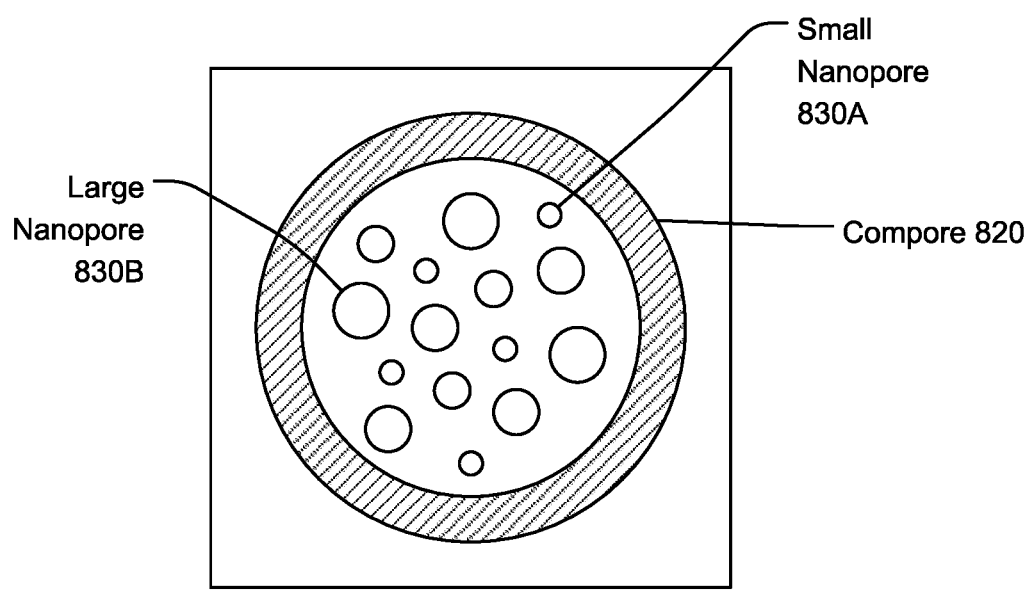
FIG. 8 is a top view showing a second alternative arrangement of nanopores within a compore.

FIG. 8 is a top view showing a second alternative arrangement of nanopores within a compore. While the compores 120 and 720 had nanopores of a consistent size, in other embodiments, the nanopores in a single compore may have different sizes. FIG. 8 depicts a compore 820 that has nanopores 830 of multiple different sizes, including a small nanopore 830A and a large nanopore 830B. The differently-sized nanopores 830 may have sloped sidewalls with the same angle (e.g., each has a sidewall angle of 10°) or different angles. In some embodiments, using multiple different sized nanopores can improve the sensitivity and dynamic range of the nanosensor.

FIG. 9 is a cross-section of a compore 900 fabricated using semiconductor technology. The structure of the compore 900 is similar to the compore shown in FIG. 3. The compore 900 includes a layer of silicon 910, which is an example of the semiconductor substrate 110. In other embodiments, other semiconductor materials may be used in place of silicon 910. Alternatively, the nanosensor can be implemented on a substrate of glass, plastic, film or other non-conducting or semiconducting material. Various etching processes may be used to thin the substrate to form the compore central regions in the silicon 910, e.g., wet etching or dry etching. A separate process such as ion-beam lithography may be used to form the nanopores. While only one compore 900 is shown in FIG. 9, multiple compores may be formed and an electrode structure laid out, as shown in FIG. 1.

Two layers of silicon nitride 920 and 930 are deposited on the top and bottom, respectively, of the silicon 910. Various deposition processes for silicon nitride may be used to deposit the two layers of silicon nitride 920 and 930, e.g., chemical vapor deposition or plasma-enhanced chemical vapor deposition. While layers of silicon nitride 920 and 930 for only one compore 900 are shown in FIG. 9, the layers of silicon nitride 920 and 930 may extend across the nanosensor chip for each of the compores included in the nanosensor chip.

Two layers of electrodes 940 and 950 are deposited on the upper layer of silicon nitride 920 and the lower layer of silicon nitride 930, respectively. The electrode layers 940 and 950 may be formed from any conductive material, e.g., copper, silver or platinum. Various deposition process for depositing the conductive material may be used to deposit the two layers of electrodes 940 and 950, e.g., evaporation or chemical vapor deposition. In this embodiment, the layers of electrodes 940 and 950 are arranged on either side of the compore 900. In other embodiments, the electrodes 940 and 950 may be laid out differently on the compore 900, as described with respect to FIG. 3. For example, in other embodiments, the electrode 940 may also be formed on the silicon sidewalls and/or on the surface of the thinned silicon. Each compore included in the nanosensor chip may have a similar electrode structure. In other embodiments, any of the electrodes may be located off-chip, in a separate component such as the chip receptacle in which the chip is mounted.

Figure 10:
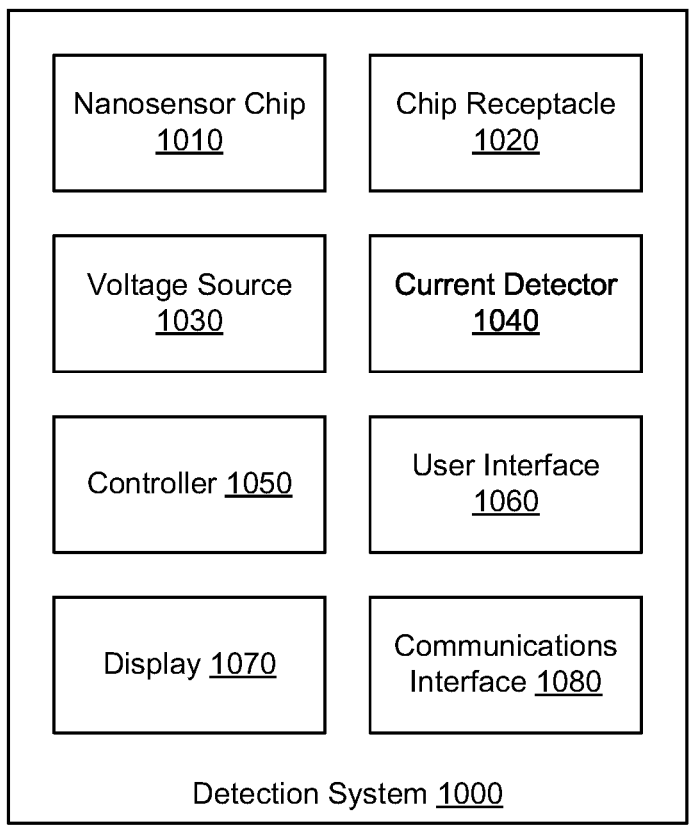
FIG. 10 is a block diagram of a detection system that includes a nanosensor chip.

FIG. 10 is a block diagram of a detection system 1000 that includes a nanosensor chip. The detection system 1000 includes a nanosensor chip 1010, a chip receptacle 1020, a voltage source 1030, a current detector 1040, a controller 1050, a user interface 1060, a display 1070, and a communications interface 1080. Other components (not shown) may include processors, memory, digital-to-analog converters, and analog-to-digital converters. In other embodiments, the detection system 1000 has additional, alternative, or fewer components than shown in FIG. 10.

The nanosensor chip 1010, as described with respect to FIGS. 1-9, has one or more compores. The chip receptacle 1020 is configured to receive and hold the nanosensor chip 1010 and form electrical connections between components of the nanosensor chip 1010 and other components of the detector system 1000. For example, the chip receptacle 1020 may include electrodes configured to connect to the electrode structures 140 shown in FIG. 1. The chip receptacle 1020 may also have one or more fluid connections to the nanosensor chip 1010, e.g., to transfer one or more liquid samples to the compores of the nanosensor chip 1010, or to transfer a buffer liquid to the compores of the nanosensor chip 1010.

The voltage source 1030 generates the electric field supplied by the electrodes to the compores. The voltage source 1030 may be a variable voltage source that generates a varying current at a range of voltages to one or more compores. In some embodiments, the voltage source 1030 is integrated into the nanosensor chip 1010. The detection system 1000 may have one voltage source 1030 or multiple voltage sources, e.g., one voltage source for each compore included in the nanosensor chip 1010. If the detection system 1000 has fewer voltage sources than compores, the nanosensor chip 1010 may have a switching mechanism to apply the voltage to one compore at a time, or the nanosensor chip 1010 may be configured to apply the same voltage to two or more compores simultaneously.

The current detector 1040 detects a current through a compore. In some embodiments, the current detector 1040 is integrated into the nanosensor chip 1010. The detection system 1000 may have one current detector 1040, e.g., one current detector for each compore included in the nanosensor chip 1010. Alternatively, it may have multiple current detectors. If the detection system 1000 has fewer current detectors than compores, the nanosensor chip 1010 may include a switching mechanism that allows the current detector to individually address a selected compore.

The controller 1050 controls the voltage source 1030 and the current detector 1040. The controller 1050 may be similar to the controller described with respect to FIG. 3. The controller 1050 may be integrated into the nanosensor chip 1050, or may be part of a separate component or device. The detection system 1000 may have one controller 1050 for controlling all of the voltage sources, current detectors, and any switching mechanisms included in the detection system 1000. Alternatively, the detection system 1000 may have multiple controllers 1050, e.g., one for each compore. In addition to controlling the voltage source 1030 and current detector 1040, the controller 1050 is also configured to interact with other components of the detection system, e.g., the user interface 1060, the display 1070, and the communications interface 1080.

The user interface 1060 is configured to receive user input, e.g., a command from a user to start an analysis of a sample, or parameters for analyzing a sample. For example, the user interface 1060 may receive parameters describing one or more voltages to be applied to a compore, or an indication of a testing procedure that is pre-programmed with a set of voltages to be run on the compore. The user interface 1060 passes these commands or parameters to the controller 1050. The user interface 1060 may include buttons, a keyboard, a touch screen, a microphone and voice recognition software, or any other suitable mechanism for receiving input from a user. Alternately, the detection system 1000 may receive commands and parameters from a mobile phone app, tablet, PC, or web application, or from an automated external control system.

The display 1070 provides visual output to a user regarding tests run by the detection system 1000. For example, the display 1070 may be used in conjunction with the user interface 1060 and the controller 1050 to display options to a user, which can be selected by the user. The display 1070 may also output test results generated by the controller 1050, e.g., whether a given target molecule is detected in a sample, or a concentration of a target molecule detected in a sample.

The communications interface 1080 may allow the detection system 1000 to communicate with one or more other devices over a network, e.g., a local network or the Internet, or by means of a serial or parallel, wireless or wired, interface such as Bluetooth, USB or other communication protocols. For example, the communications interface 1080 may upload results of a test performed by the detection system 1000 to another device or component for further processing, or may upload test results to a database.

Upon reading this disclosure, those of skill in the art will appreciate still additional alternative structural and functional designs for a nanosensor chip and detection system. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the apparatuses disclosed herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

What is claimed is:

1. A method for detecting a target nucleic acid molecule, comprising:
    (a) providing a nanosensor chip comprising a compore, wherein said compore comprises a plurality of nanopores, wherein each nanopore of said plurality of nanopores individually comprises a plurality of probe molecules immobilized thereto, wherein a nanopore of said plurality of nanopores comprises a probe molecule of said plurality of probe molecules that has a binding specificity to said target nucleic acid molecule;
    (b) directing a solution containing or suspected of containing said target nucleic acid molecule to said nanosensor chip and applying a varying voltage over time on said plurality of nanopores including said nanopore to permit said target nucleic acid molecule to bind to said probe molecule at a selected voltage of said varying voltage;
    (c) measuring simultaneously from said plurality of nanopores of said compore current signals or changes thereof over said time to generate an aggregate current or change thereof over said time as an output, wherein said aggregate current or change thereof over said time is indicative of said target nucleic acid molecule binding to said probe molecule; and
    (d) using said output measured in (c) to detect said target nucleic acid molecule.

2. The method of claim 1, wherein said target nucleic acid molecule is a ribonucleic acid (RNA) molecule, or deoxyribonucleic acid (DNA) molecule.

3. The method of claim 1, further comprising using one or more electrodes to apply an electric field across said plurality of nanopores, and wherein said electric field modulates an interaction between said target nucleic acid molecule and said probe molecule.

4. The method of claim 1, further comprising using one or more electrodes to measure said output.

5. The method of claim 1, wherein (c) is performed in a presence of one or more blocked or clogged nanopores of said plurality of nanopores.

6. The method of claim 1, wherein said probe molecule is configured to reversibly bind to said target nucleic acid molecule.

7. A method for detecting a first target nucleic acid molecule and a second target nucleic acid molecule, comprising:
    (a) providing a nanosensor chip comprising a compore, wherein said compore comprises a plurality of nanopores, wherein a first nanopore of said plurality of nanopores comprises a first probe molecule immobilized thereto, wherein said first probe molecule has a binding specificity to said first target nucleic acid molecule, and wherein a second nanopore of said plurality of nanopores comprises a second probe molecule immobilized thereto, wherein said second probe molecule has a binding specificity to said second target nucleic acid molecule, wherein said first target nucleic acid molecule and said first probe molecule bind under different conditions from said second target nucleic acid molecule and said second probe molecule;
    (b) directing a solution containing or suspected of containing said first target nucleic acid molecule or said second target nucleic acid molecule to said nanosensor chip and applying a varying voltage over time on said plurality of nanopores including said first nanopore and said second nanopore to permit said first target nucleic acid molecule to bind to said first probe molecule at a first voltage of said varying voltage or said second target nucleic acid molecule to bind to said second probe molecule at a second voltage;
    (c) measuring, simultaneously from said plurality of nanopores, current signals or changes thereof over said time to generate an aggregate current or change thereof over said time as an output, wherein said aggregate current or change thereof over said time is indicative of said first target nucleic acid molecule binding to said first probe molecule or said second target nucleic acid molecule binding to said second probe molecule; and (d) using said output measured in (c) to detect said first target nucleic acid molecule or said second target nucleic acid.

8. The method of claim 7, wherein said solution comprises a plurality of different target nucleic acid molecules which comprises target nucleic acid molecules other than said first target nucleic acid molecule and said second target nucleic acid molecule.

9. The method of claim 7, further comprising applying a voltage across said compore.

10. The method of claim 9, wherein said voltage varies over time, and wherein (c) further comprises measuring said voltage or a change thereof.

11. The method of claim 7, wherein said first voltage is different from said second voltage.

12. The method of claim 7, wherein said first probe molecule or said second probe molecule independently comprise a nucleic acid molecule, a polymer, or an oligonucleotide.

13. The method of claim 1, wherein said output averages out variation in a concentration of said target nucleic acid molecule by detecting said output over said plurality of nanopores.

14. The method of claim 1, wherein said nanopore comprises a sloped sidewall and wherein said probe molecule is immobilized to said sloped sidewall of said nanopore.

15. A method for detecting a target molecule, comprising:
(a) providing a nanosensor chip comprising a compore, wherein said compore comprises a plurality of nanopores, wherein each nanopore of said plurality of nanopores comprises a probe molecule immobilized thereto, wherein said probe molecule has a binding specificity to said target molecule;
(b) directing a solution containing or suspected of containing said target molecule to said nanosensor chip and applying a varying voltage over time on said plurality of nanopores to permit said target molecule to bind to said probe molecule at a selected voltage of said varying voltage;

(c) measuring simultaneously from said plurality of nanopores of said compore current signals or changes thereof over said time to generate an aggregate current or change thereof over said time as an output, wherein said aggregate current or change thereof over said time is indicative of said target molecule binding to said probe molecule; and (d) using said output measured in (c) to detect said target molecule.

16. The method of claim 15, wherein (c) is performed in a presence of one or more blocked or clogged nanopores of said plurality of nanopores.

17. The method of claim 15, further comprises detecting a concentration of said target molecule based on said output.

18. The method of claim 15, wherein said target molecule comprises antibodies, antibody analogs, proteins, aptamers, polymers, contaminants, or nanobodies.

19. The method of claim 1, further comprising using a pair of electrodes corresponding to said compore to perform said measuring.

20. The method of claim 1, wherein said aggregate current or change thereof is a single output.

21. The method of claim 1, further comprising, during (c), measuring said aggregate current or change thereof during a binding of said nucleic acid molecule to said probe.

22. The method of claim 7, further comprising using a pair of electrodes corresponding to said compore to perform said measuring.

23. The method of claim 7, wherein said aggregate current or change thereof is a single output.

24. The method of claim 7, further comprising, during (c), measuring said aggregate current or change thereof during a binding of said nucleic acid molecule to said probe.

25. The method of claim 15, further comprising using a pair of electrodes corresponding to said compore to perform said measuring.

26. The method of claim 15, wherein said aggregate current or change thereof is a single output.

27. The method of claim 15, further comprising, during (c), measuring said aggregate current or change thereof during a binding of said target molecule to said probe.

28. The method of claim 1, wherein said each nanopore of said plurality of nanopores comprises a plurality of a same probe molecule immobilized thereto.

* * * * *